United States Patent
Romans

(10) Patent No.: US 8,229,762 B2
(45) Date of Patent: *Jul. 24, 2012

(54) SYSTEM AND METHOD FOR CARDIOVASCULAR TESTING

(75) Inventor: John A. Romans, North Oaks, MN (US)

(73) Assignee: BioMedix, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/181,959

(22) Filed: Jul. 13, 2011

(65) Prior Publication Data

US 2011/0270626 A1 Nov. 3, 2011

Related U.S. Application Data

(63) Continuation of application No. 10/227,770, filed on Aug. 26, 2002, now Pat. No. 7,983,930.

(60) Provisional application No. 60/314,907, filed on Aug. 24, 2001.

(51) Int. Cl.
*G06Q 10/00* (2006.01)
*G06Q 50/00* (2006.01)

(52) U.S. Cl. .................... 705/2; 705/3; 600/300

(58) Field of Classification Search .......... 705/2–4; 600/300; 128/903, 904; 455/404.1
See application file for complete search history.

(56) References Cited

U.S. PATENT DOCUMENTS

| | | | |
|---|---|---|---|
| 5,822,544 A | 10/1998 | Chaco et al. | |
| 5,823,948 A | 10/1998 | Ross, Jr. et al. | |
| 6,024,699 A | 2/2000 | Surwit et al. | |
| 6,364,834 B1 * | 4/2002 | Reuss et al. | 600/300 |
| 6,804,656 B1 * | 10/2004 | Rosenfeld et al. | 705/3 |
| 7,103,578 B2 | 9/2006 | Beck et al. | |
| 7,383,358 B1 | 6/2008 | Kennedy | |
| 7,464,040 B2 * | 12/2008 | Joao | 705/2 |
| 2004/0049355 A1 | 3/2004 | Maus et al. | |

* cited by examiner

*Primary Examiner* — Michelle Le
(74) *Attorney, Agent, or Firm* — Kinney & Lange, P.A.

(57) ABSTRACT

A system for testing and diagnosis of a medical condition includes a test device located at a test location and configured to perform a medical testing protocol for generating test data, and a recipient computer for receiving the patient data from the test device. The test device includes a computer and memory module for storing a patient record containing test data and a communications module for sending the patient record to a medical specialist. The test data comprises vascular test data. The recipient computer displays the test data to the medical specialist at a diagnosis center located remote from the test location. The recipient computer includes an input device configured to enter input indicative of a diagnosis by the medical specialist as a function of medical analysis of the test data. The input indicative of the diagnosis includes an electronic signature executed by the medical specialist.

4 Claims, 13 Drawing Sheets

PATIENT DEMOGRAPHIC INFORMATION                                        ☒

| Last Name: | DOE | Address: | |
|---|---|---|---|
| First Name: | JOHN | City, State: | |
| Patient I.D. | | Medication: | |
| Referring Dr: | | Height: R [ ] In:[ ] Weight(lbs):[ ] | |
| Attending Dr: | | Sec [M] Age: [56] | |
| Patient Location: | | | |
| Date Of Birth: | 11/11/1945 | Soc Sec Number [213/21/3213] [1] | |

| F1-SAVE ENTRIES | F2-ESCAPE | F3- PREV CONDITIONS | F4-IMPRESSIONS | F5-SYMPTOMS | F6-PHYSICAL SIGNS |

Click Here To Enter The Patients Previously Diagnosed Conditions

Fig. 5

DIAGNOSED CONDITIONS                                                  ☒

| Diabetes: [1] | Years: [ ] |
|---|---|
| Hypertension: [ ] | Years: [ ] |
| Hyperlipidemia: [ ] | Family History: [ ] |
| Angina: [ ] | Syncope: [ ] |
| Stroke/TIA: [ ] | Vericose Veins: [ ] |
| Heart Disease: [ ] | |
| Previous Vascular Surgery: [ ] | Bruit: [ ] |

[F1. TO PREVIOUS SCREEN]

Fig. 6

| PHYSICAL SIGNS AND SYMPTOMS | | | | Pale Location | | |
|---|---|---|---|---|---|---|
| | LEFT | RIGHT | | | LEFT | RIGHT |
| Rest Pain: | ☐ | ☐ | Thigh/Buttock | | ☐ | ☐ |
| Claudication | ☐ | ☐ | Calf | | ☐ | ☐ |
| Swollen Ankle | ☐ | ☐ | Arch | | ☐ | ☐ |
| Cold Foot | ☐ | ☐ | Toe | | ☐ | ☐ |
| Phlebitis | ☐ | ☐ | Pain Relieved By: | | | |
| Vein Problems | ☐ | ☐ | Rest | | ☐ | ☐ |
| | | | Exercise | | ☐ | ☐ |
| | | | Legs Elevated | | ☐ | ☐ |
| | | | Legs Down | | ☐ | ☐ |

F1. TO PREVIOUS SCREEN

Fig. 9

Vascular Report Generator
Set Custom Protocol

SERIES
LOWER EXTREMITY ARTERIAL
LOWER EXTREMITY ARTERIAL
LOWER EXTREMITY VENOUS
UPPER EXTREMITY ARTERIAL
UPPER EXTREMITY DIGIT
LOWER EXTREMITY DIGIT
CEREBROVASCULAR
UROLOGY

F5. Show Next Location
Click Here To Show The Mode/Location of the Next Test in the Protocol
Protocol Name  DEFAULT PROTOCOL Protocol List
DEFAULT PROTOCOL F1. Exit and Save   F2. Add Protocol   F3. Delete Protocol   F4. Save Location

Fig. 10

SYSTEM AND METHOD FOR CARDIOVASCULAR TESTING

CROSS-REFERENCE TO RELATED APPLICATIONS

This application is a continuation of U.S. patent application Ser. No. 10/227,770 filed Aug. 26, 2002 entitled SYSTEM AND METHOD FOR TESTING FOR CARDIOVASCULAR DISEASE, now U.S. Pat. No. 7,983,930, and claims priority from U.S. Provisional Patent Application 60/314,907 filed Aug. 24, 2001 entitled CARDIOVASCULAR DISEASE DIAGNOSTIC METHOD. Said applications are incorporated herein by reference.

TECHNICAL FIELD

The present invention relates to the field of medical diagnostics and more particularly to devices and methods for measuring attributes of human body systems.

BACKGROUND OF THE INVENTION

Cardiovascular disease is the number one killer in the United States. According to the American Heart Association, cardiovascular disease inflicts over 59 million Americans and contributes to approximately sixty percent of all deaths recorded each year. This deadly disease attacks both men and women, equaling the next seven leading causes of death combined for men and causing one out of every two deaths in women. Treatment options for cardiovascular disease are continuing to expand. However, patients are often diagnosed too late to be treated effectively or without invasive measures. Accordingly, early diagnosis and early treatment are vital to ensure successful outcomes.

To date, tools for obtaining such an early diagnosis have been difficult to access. Typically, devices for measuring blood flows through arteries and veins (which are necessary for diagnosing cardiovascular disease) are large and expensive. Further, interpretation of the results of such testing require the doctor performing such tests to have special skills. As a result, such testing is usually performed only in vascular laboratories in large hospitals. Here, the cost of having equipment and the necessary doctor expertise can be justified through the volume of patients using such equipment. Yet a patient may not go to a hospital until the cardiovascular disease has progressed to an advanced stage. Accordingly, it is desirable to perform such tests on a more routine basis.

SUMMARY OF THE INVENTION

A system for testing and diagnosis of a medical condition according to the present invention includes a test device located at a test location and configured to perform a medical testing protocol for generating test data, and a recipient computer for receiving the patient data from the test device. The test device includes a computer and memory module for storing a patient record containing test data and a communications module for sending the patient record to a medical specialist. The test data comprises vascular test data. The recipient computer displays the test data to the medical specialist at a diagnosis center located remote from the test location. The test location and the diagnosis center are located at different facilities. The recipient computer includes an input device configured to enter input indicative of a diagnosis by the medical specialist as a function of medical analysis of the test data. The input indicative of the diagnosis includes an electronic signature executed by the medical specialist.

BRIEF DESCRIPTION OF THE DRAWINGS

FIGS. 4-9 are patient data entry screens of the computer.
FIGS. 10-12 are testing setup screens.

DETAILED DESCRIPTION OF THE INVENTION

The present invention is a system and method for performing testing for cardiovascular disease. A test unit is used to measure parameters related to blood flow in a patient. The test unit stores the test data in association with a patient record containing patient data. The test unit is preferably a low cost unit that can be located at a general practitioner's office so that the testing can be performed as a routine part of the general practitioner's care.

Once the testing is done, the patient record including the test data is then transmitted to a diagnostic center for review and any necessary diagnosis. The diagnosis center could be physically remote from the testing unit, for example at a hospital. By setting up a number of test units at varied locations with the test data being sent to diagnosis centers, the frequency of tests can be increased while still having diagnosis performed by experts. The result is increased and accurate testing for cardiovascular disease.

In a preferred embodiment, the patient record is routed to a diagnosis unit that performs predefined diagnosis tests on the test data. The diagnosis tests then prepare a report for expert review and confirmation.

In a further preferred embodiment, the patient record is routed to a payer center that can receive information regarding the performance of a medical test and process payment for the testing based upon the patient's insurance coverage.

An intermediate computer can be used to route records from a test center to a diagnosis center and/or a payer center. The intermediate computer can strip information from a patient record so that only necessary information is sent to the diagnosis center and the payer center. The intermediate computer may also store and execute diagnostic routines for ensuring the proper operation of the medical testing equipment at the test centers.

Figure 1:
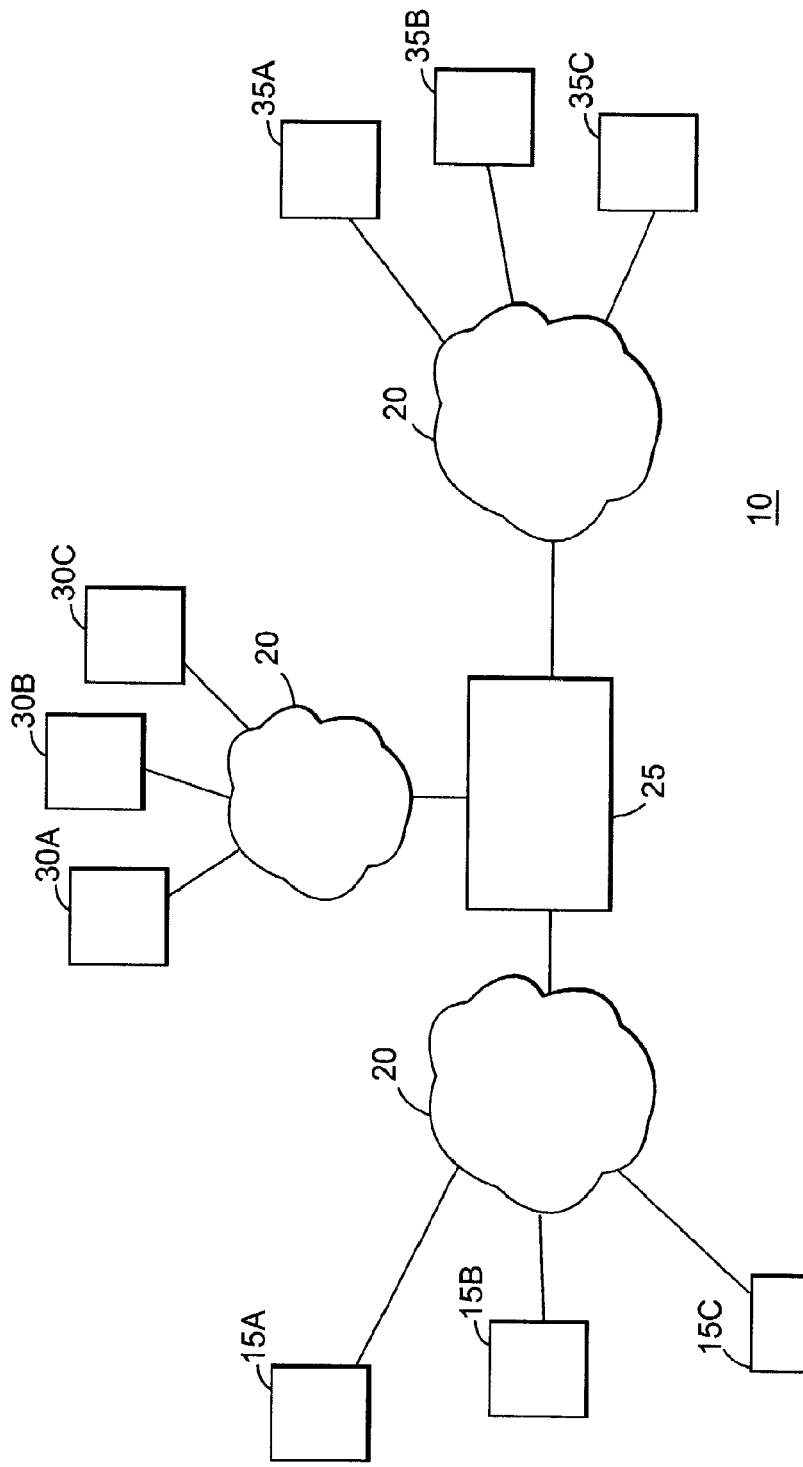
FIG. 1 is a block diagram of the inventive system.

Referring now to FIG. 1, thereshown is a testing system 10 of the present invention. Test units 15A-C may be located at multiple locations, such as at doctors' offices. The test units may include medical testing devices such as an electronic sphygmomanometer coupled to a computer. The computer is setup to store patient records including test data produced by the medical testing devices. The test units are connected to the public communications network 20 including the telephone network, the internet and other dedicated electronic communication facilities. In a preferred embodiment, the test data is sent to an intermediate server 25 for holding. Diagnosis centers 35 A-C can connect to the intermediate server to download the test data for analysis.

Alternatively, the test unit may send the test data to the intermediate server via e-mail and the intermediate server may then forward the e-mail to a selected diagnosis center. In still another alternative embodiment, a direct connection via the public communications network 20 could be established between the test unit and the diagnosis center. In summary, there are many methods of communication between the test unit and the diagnosis unit.

In addition, the system can be used to automatically seek and obtain payment for the testing from appropriate insurance providers (as available), the intermediate server may be connected via the public communications network to payers (which may be insurance companies) 30A-C.

Figure 2:
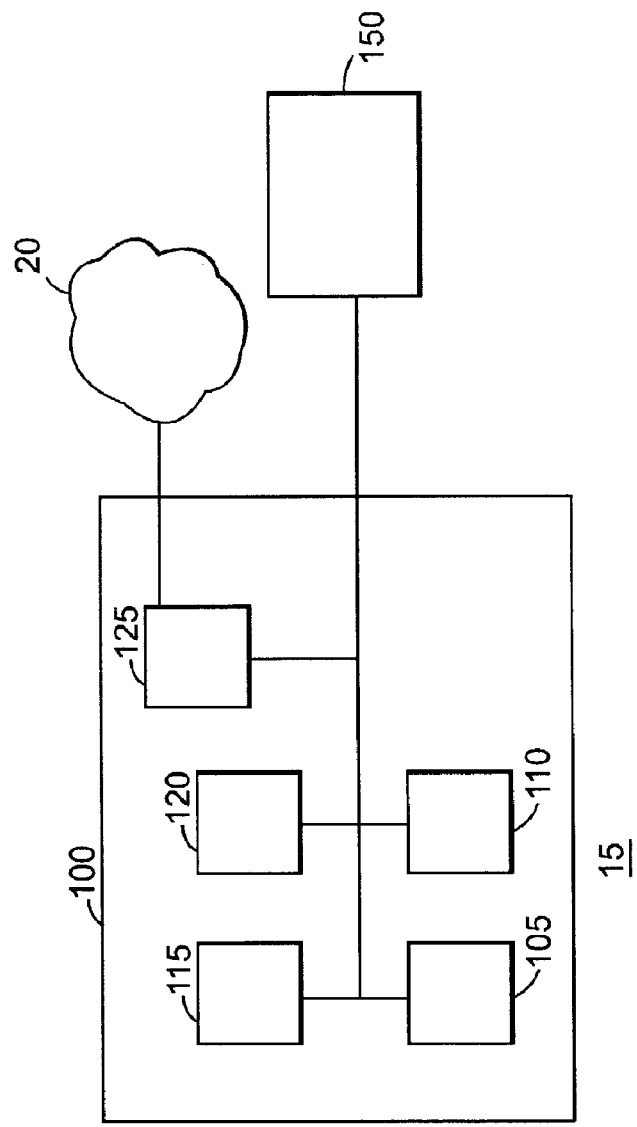
FIG. 2 is a block diagram of a test unit of the presently inventive system.

Shown is FIG. 2 is a block diagram of a test unit. In a preferred embodiment, the test unit comprises a computer 100 and a medical test system such as an electronic sphygmomanometer. In operation, the computer can be used to track data associated with the patient, the doctor and the test being performed. The computer 100 is also programmed to control the operation of the medical test system. The computer has a central processing unit (CPU) 105, a data entry device such as a keyboard 110, a memory 115, a display 120 and an external communications device (such as a network card or a modem) 125. The medical test system 150 is connected to the computer and provides data to the computer for storage in memory 115. In particular, memory 115 may hold a database of patients along with associated personal and test data. Note however that the specific construction of the computer is not limited to the disclosed structure. Many other structures of computer will still fall within the spirit of the present invention.

Figure 3:
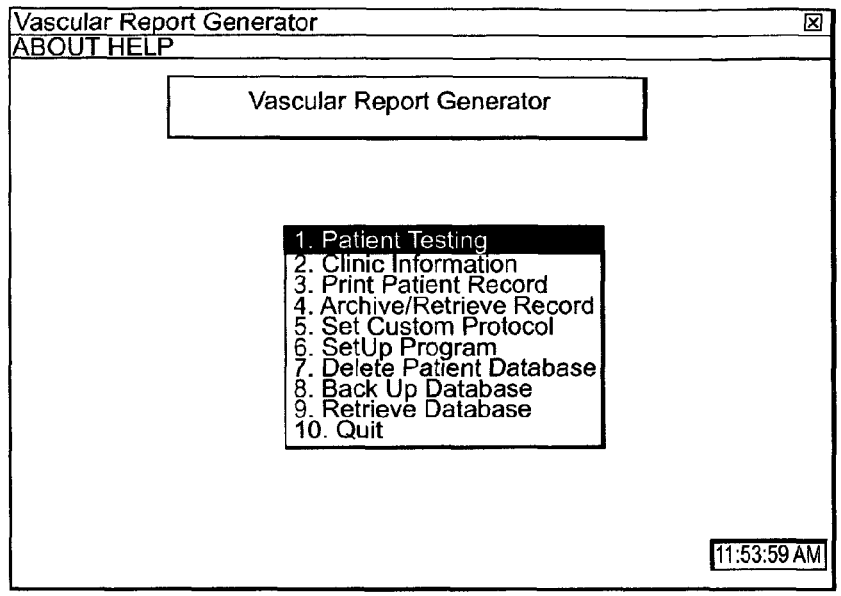
FIG. 3 is a screen display of a computer used as part of the test unit.

Referring now to FIG. 3, thereshown is a screen print of a computer driven menu of a test unit 15. As can be seen, many choices are available to the operator of the test unit. On the selection of the patient testing option, a screen such as the one shown in FIG. 4 may be displayed.

Figure 4:
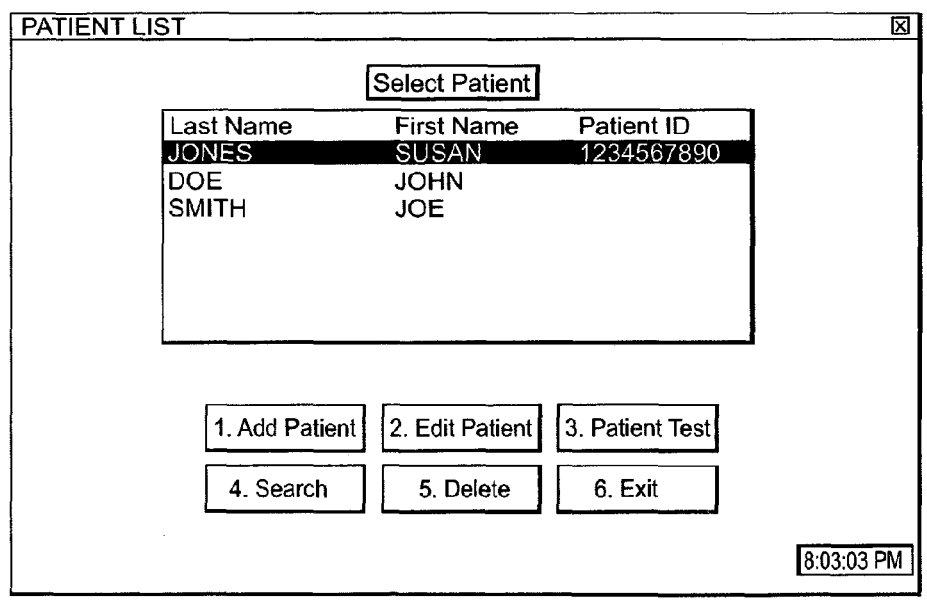

In FIG. 4, a user of the test unit would be given the option of adding a patient record to a database, editing a patient record already in the database, testing a selected patient, searching for selected information, deleting a patient record from the database, or exiting from the screen.

If the user selects the add a patient option, the test unit may then display the screen shown in FIG. 5 so that the user can setup a patient record. At this screen, the user is offered the opportunity to enter data about the patient, such as last name, first name, a patient identification number, name of a referring doctor, name of an attending doctor, patent location, patient address including city and state, a list of any medications the patient is currently taking, patient height, patient weight, sex and age of the patient and the patient's social security number. Not shown but also included in patient data entry is the patient's medical insurance information. Many other fields may be entered for tracking of desired information.

Figures 7, 8:
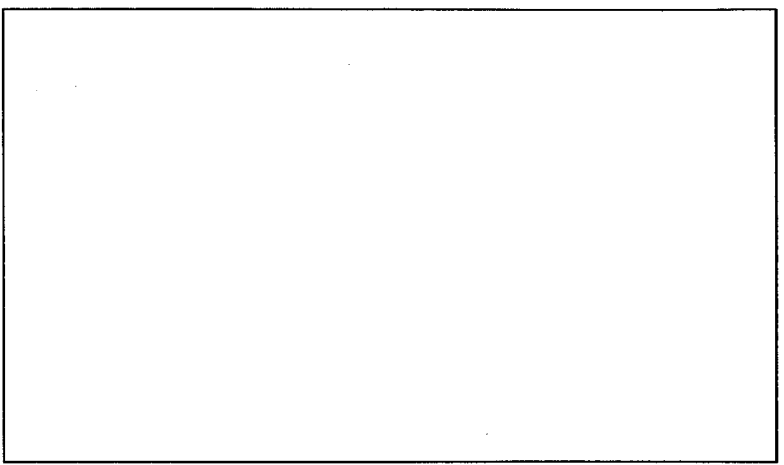

Further patient record information may be entered in connection with FIGS. 6-9. FIG. 6 is a screen print of another patient data entry screen at which data associated with previously diagnosed conditions of the patient may be entered. In FIG. 7, the user is given the opportunity to enter comments into the patient's record. In FIG. 8, the user may enter symptoms experienced by the patient and risk factors associated with the patient into the patient's record. FIG. 9 shows a screen at which physical signs and symptoms may be entered into the patient's record.

Once a patient record has been created, a specific test series can be entered for a patient as shown in FIG. 10. As examples, a number of different test protocols may be stored in the computer. In the present example, the possible test protocols are a Lower Extremity Arterial, Lower Extremity Venous, Upper Extremity Arterial, Upper Extremity Digit, Lower Extremity Digit, Cerebrovascular and Urology. A user would select a desired test and test data would then be set up accordingly. Here, a Lower Extremity Arterial test is selected.

Figure 11:
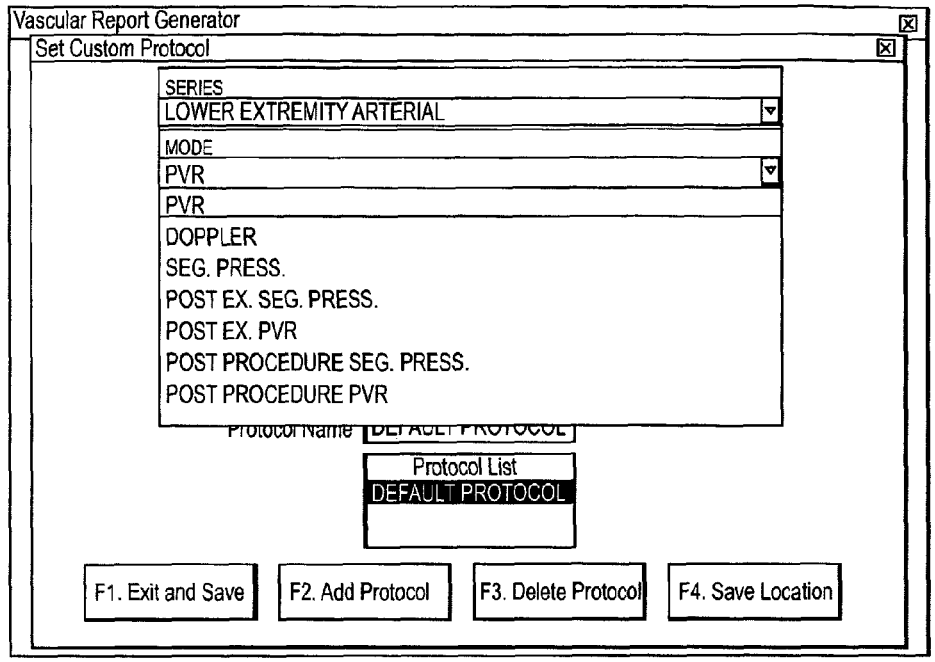

In FIG. 11, the type of sensing or mode, may be selected. In the present example, PVR or Pulse Volume Recording is selected. Other methods can include Doppler, Segment Pressure, Post Examination Segment Pressure, Post Examination PVR, Post Procedure Segment Pressure and Post Procedure PVR.

Figure 12:
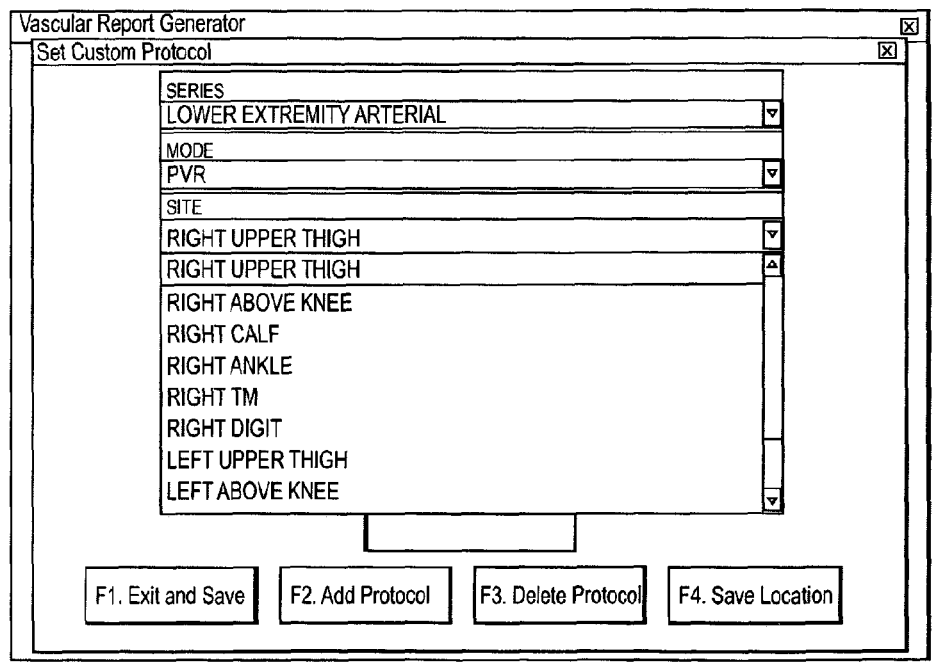

Once the test protocol and mode are selected, the body location being tested may be selected. The data entry screen for such selection is shown in FIG. 12. The body part list being presented may depend from the series of tests that has been selected. For the Lower Extremity Arterial test, the location of the test could be at least the Right Upper Thigh, Right Leg above the Knee, Right Calf, Right Ankle, Right Foot, Toe on Right Foot, and the same locations on the left side.

Figures 13, 14:
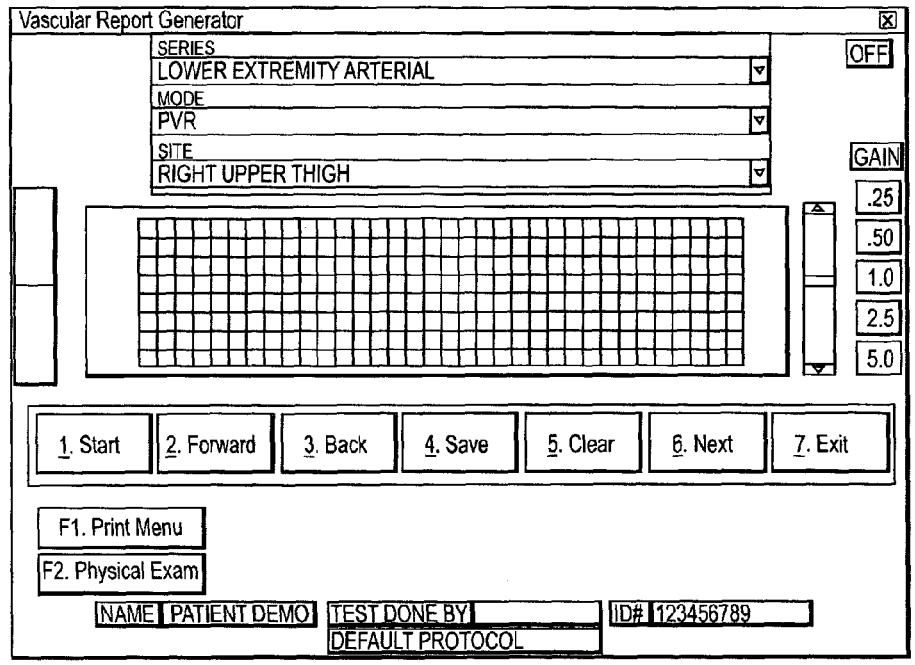
FIG. 13 is a test data display screen.
FIG. 14 is a physical exam data entry screen.

Referring now to FIG. 13, thereshown is an exemplary display of a test result screen. In particular, once a test has begun, results may be plotted on the grid area of the screen for displaying of measured test parameters. In FIG. 14, results from a physical examination of, for example, pulse at a number of locations may be entered into the patient's record to be associated with a set of test data.

Figure 15:
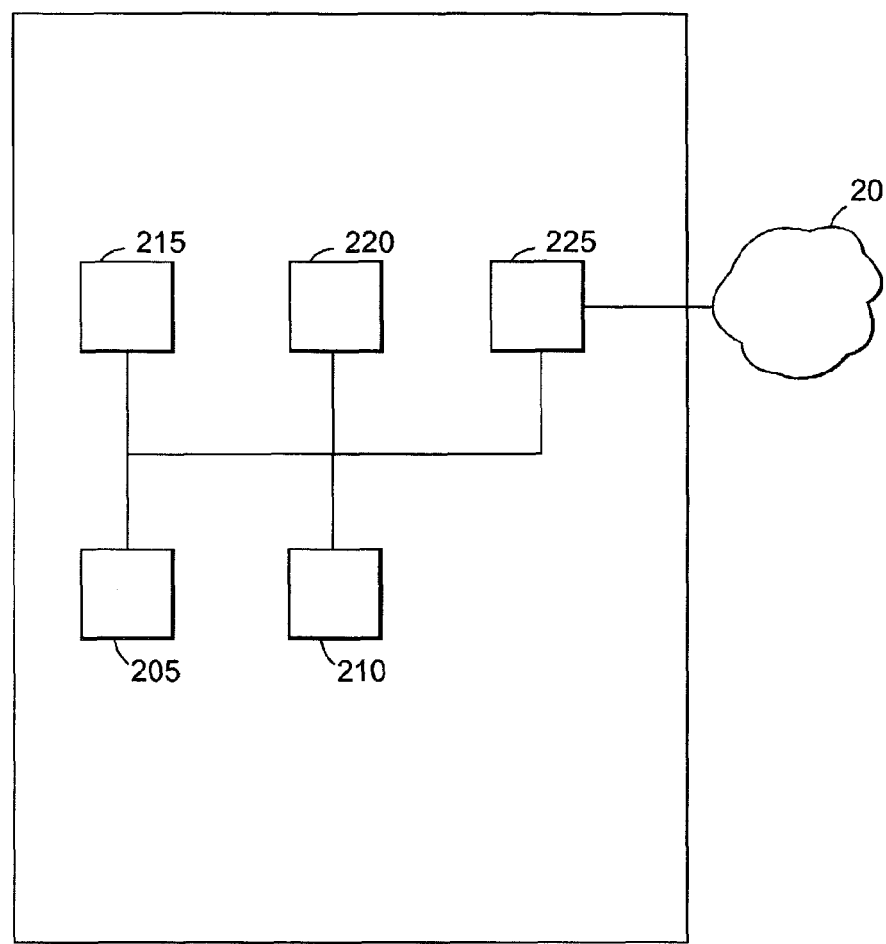
FIG. 15 is a block diagram of the intermediate computer.

Referring now to FIG. 15, thereshown is a preferred embodiment of the intermediate server 25. The computer has a central processing unit (CPU) 205, a data entry device such as a keyboard 210, a memory 215, a display 220 and an external communications device (such as a network card or a modem) 225.

The intermediate computer may perform a number of different functions including storage of received patient records, transmission of all or part of patient records to a diagnosis center, transmission of all or part of patient records to payers, tracking of testing statistics (e.g. tests performed by site, diagnoses done per site, payments made by site), performing diagnostic checks on test units and the like. Note however that the specific construction of the computer is not limited to the disclosed structure. Many other structures of computer will still fall within the spirit of the present invention.

One of the important functions performed by the intermediate computer in a preferred embodiment of the invention is to remotely assume control of the test unit at the general practitioner's site by controlling the computer in the test unit. Such remote control allows the technical support personnel at the intermediate computer to remotely provide assistance to an operator of the test unit at the general practitioner's site. Typically, an operator using the test unit has training as an end-user of the unit but may from time to time need technical help from the experts at the test unit provider. For example, when an operator encounters difficulties using the test unit, technical support personnel can take over the control of the test unit and be able to determine the cause of the difficulties, resolve the difficulties and return the control back to the operator. Such a mode of operation can drastically reduce the number of resources in the field needed by the test unit provider and thus result in a more economical operation of the entire system.

The remote control can be achieved by any suitable scheme well known in the art. For example, a remote display system known as the "Virtual Private Network", or "VPN" can be used to allow a person at the intermediate computer to take over the test unit after permission for such control is granted by an authorized person at the test unit.

Figure 15A:
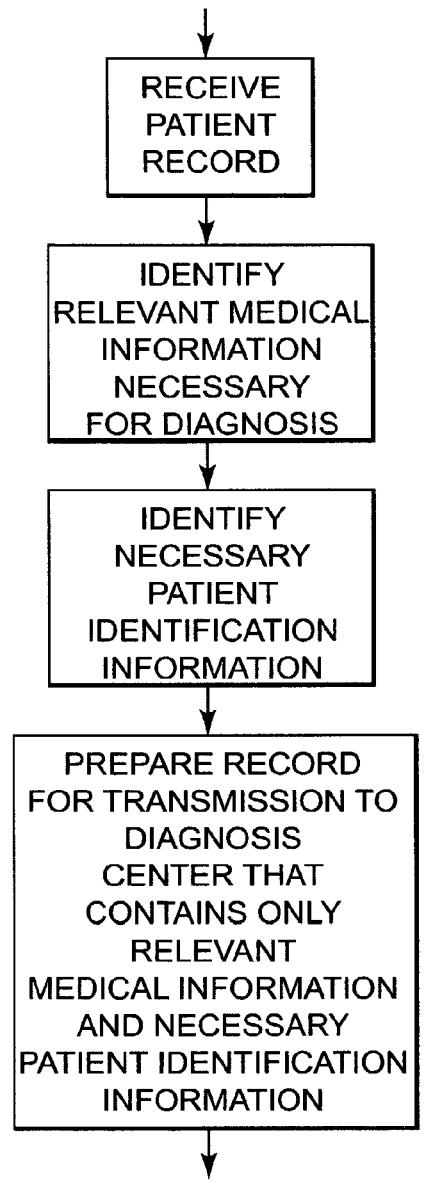
FIG. 15A is a flow chart of a preferred record creation process for records to be transmitted to a diagnosis center.

Each patient record will include test data from a test. In one preferred embodiment, the intermediate computer will transmit the test data along with patient identifying information to a diagnosis center. While all of a patient record may be shipped to a diagnosis center with each test being diagnosed, in a preferred embodiment, only a limited set of patient identifying information, along with all relevant medical information will be sent. The information from a patient record that is forwarded on to a diagnosis center could be preselected for each type of test. This structure allows for efficient use of communications assets and assists in the maintenance of privacy of patient data. This process is shown in FIG. 15A. While the steps in FIG. 15A are shown as in a sequence, this provided by way of example, not limitation. As one alternative, the necessary patient identification information may be selected before the relevant medical information or they may be selected in parallel. The spirit of the invention requires selection of this information, not a particular order for the selection.

Figure 15B:
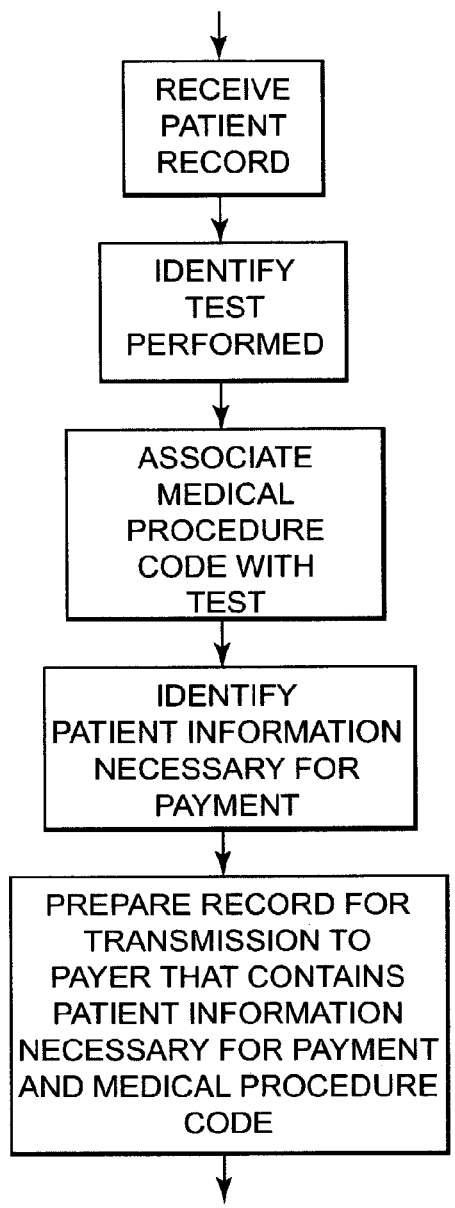
FIG. 15B is a flow chart of a preferred record creation process for records to be transmitted to a payer center.

The patient record will also contain information about performance of a test that was the reason the patient record was sent to the intermediate computer. In a preferred embodiment, on receipt of a patient record, the intermediate server 25 analyzes the patient record, identifies tests that have been performed, the doctor performing the test, and the insurance company associated with the patient. The intermediate computer, in a preferred embodiment, stores a database of medical procedure codes and associates a medical procedure code with the test performed. Thereafter, the intermediate server may automatically notify the insurance company of the receipt of a record requiring the company's attention. Alternatively, the intermediate server could store information about the new record to be shipped to the insurance company upon a request to the intermediate server to do so. This process is shown in the flow chart of FIG. 15B. As in FIG. 15A, while the elements of FIG. 15B are shown in a sequence, this is provided by way of example, not limitation. As one alternative, the necessary patient identification information may be selected before the identification of the relevant medical procedure code or they may be selected in parallel. The spirit of the invention requires selection of this information, not a particular order for the selection.

A still further function of the intermediate computer 25 may be to perform diagnostics on test units 15 and in particular on medical test devices 150. The intermediate computer 25 may store test routines that can be performed by a trained expert through connection to the test unit 15. In particular, a direct dial up connection, a network connection through software such as PC Anywhere software, or a web interface connection could be used to have the test unit perform certain functions and report results back to the intermediate computer.

Another function of the intermediate computer 25 can be to provide training remotely to the end-users of the medical test devices 150. Training can be provided in a number of effective ways. One approach is installing an automated training program on the intermediate computer 15, which the end-users can remotely access to download lessons. Another approach is to have live training, with the trainer illustrating the operations by controlling the trainee's testing unit as discussed above.

Figure 16:
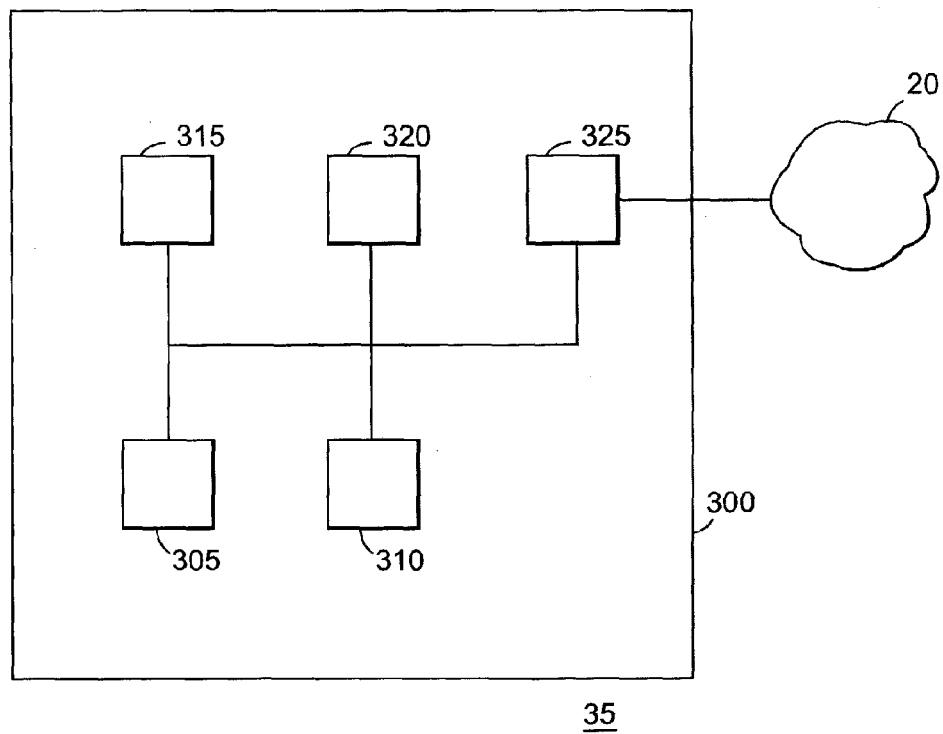
FIG. 16 is a block diagram of a diagnosis center.

Referring now to FIG. 16, there shown is a preferred embodiment of a diagnosis center 35 which may include a computer 300 with a connection to the public communications network 20. Computer 300 may include a central processing unit (CPU) 305, a data entry device such as a keyboard 310, a memory 315, a display 320 and an external communications device (such as a network card or a modem) 325. The diagnosis center may either receive records sent from the intermediate computer, may connect to the intermediate computer through the public communications network 20 or may receive records through a direct connection to a test center 15.

Upon receipt of a record, the intermediate computer at the diagnosis center forwards the record to a diagnostician for interpretation of the record. The forwarding process can be carried out in a variety of well-known ways. For example, the intermediate computer may simply notify a diagnostician that a record has arrived at the diagnosis center. The diagnostician can then indicate whether he or she will take the case, and if he or she does, download a copy of the record.

A diagnostician can provide diagnosis based on the record in any suitable manner. For example, in an automated and paperless process, a diagnostician can fill out an electronic record analysis form that accompanies the record based on his or her review of the record.

After a diagnostician has completed his or her analysis of the record, he or she can then transmit the analysis back to the general practitioner who provided the record. Under typical medical insurance systems, such analyses are legal documents that must be validly executed by the physicians performing the analyses. Thus, according to one aspect of the invention, the diagnosticians are provided with computers that are equipped with signature recorders that are capable of biometric recognition. Thus, an electronic diagnosis form electronically signed by a diagnostician is compliant with the Health Insurance Portability and Accountability Act (HIPAA). Such signature recorders are well known and have numerous applications, such as credit card authentication.

It should be pointed out that the invention enables the efficient management of a highly flexible diagnostic service system. The test devices need not to be identical; in fact, they can be devices for diagnosing entirely different medical conditions. Correspondingly, diagnosticians of a diverse set of specialties can be enlisted to interpret the test data. The intermediate computer thus can also serve as a manager that directs work flow by routing requests for interpretation to the appropriate diagnosticians depending on the originating test device. The information on the types of tests each device is capable of making and the appropriate diagnosticians can be stored in a database associated with the intermediate computer as a basis for determining diagnostic work flow.

Figure 17:
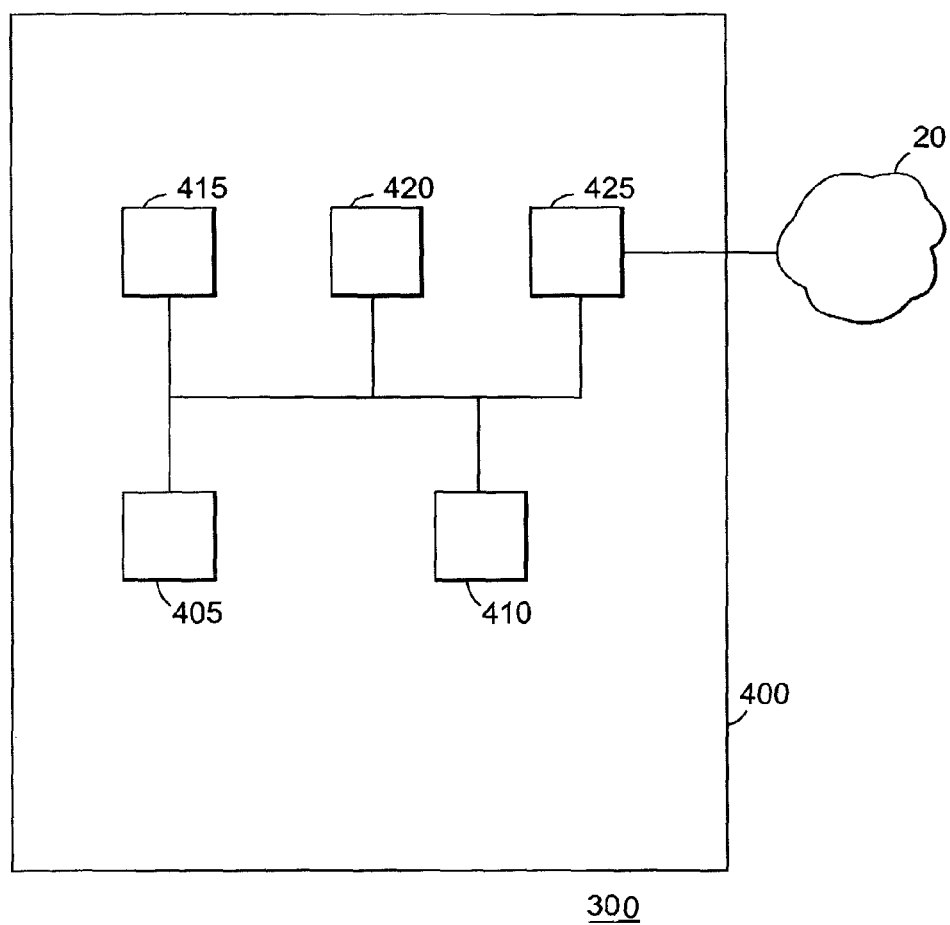
FIG. 17 is a block diagram of a payer center.

Referring now to FIG. 17, there shown is a preferred embodiment of a billing center 300 which may include a computer 400 with a connection to the public communications network 20. Computer 400 may include a central processing unit (CPU) 405, a data entry device such as a keyboard 410, a memory 415, a display 420 and an external communications device (such as a network card or a modem) 425. The diagnosis center may either receive records sent from the intermediate computer, may connect to the intermediate computer through the public communications network 20 or may receive records through a direct connection to a test center 15.

The billing center computer may store itself or be connected to other computing resources from which information about the patient may be recalled. For example, the billing center may store information about the patient's prior medical history, recent tests, level of coverage, deductible, year to date payments, ordinary and customary payment levels, lifetime payment limits and other factors affecting coverage.

In a preferred embodiment, the billing center computer manages bills sent to payers by optimizing either electronic or paper filings with the appropriate payer. The billing center computer receives billing information from the parties (e.g., testers and interpreters) seeking payments from the payers (e.g., insurance carriers) for the medical services rendered. Such billing information typically includes payer information, patient identification, a description of services rendered and amount billed for the services. The description of services rendered can be in the form of a set of predefined codes. The billing center computer then transmits the billing information to the appropriate payers, or sends a payment request notice to the payers and provides the payers access to the details of billings at the billing center computer.

Each payer may have its own system for determining the amount of payment. Upon receipt of a record requesting payment, payers may access information from the billing center to determine the payment amount to be paid. The payers can then send reimbursements directly to the testers and interpreters.

In a further embodiment, the billing center computer can also manage billing for the diagnostic system services provided to the test and interpretation participants. This is performed by tracking the number of tests performed on a periodic basis and invoicing based on a service agreement in place with each interpreter and tester.

In another embodiment, wireless technology is employed to further enhance the system performance. For example, commercial wireless services such as Blue Tooth™ can be used to facilitate automatic test data transfer. In particular, portable field test devices can include wireless receivers and transmitters. A base unit including a computer, radio frequency beacon and receivers can be installed at a physician's clinic. When a test device is brought back from the field (such as patient's homes) to the clinic, the receiver on the test device detects the beacon and subsequently causes the transmitter to transmit a signal indicating the presence of the test device. Upon the receiver of the base unit detecting the signal, the base unit computer begins a wireless download of the test data and transfer the downloaded date to the intermediate computer. Thus, the transmission of test data for diagnostic interpretation is automated.

The invention optimizes the process of providing medical diagnostic services. It utilizes computers and computer networks to economically place diagnostic devices where they are the most effectively used while placing the data produced by these devices within easy reach of the expert interpreters of the data. The efficiency and quality of service is enhanced by such features as remote control and troubleshooting of the test devices, remote training and centralized billing process. As a result, satisfactory financial arrangements can be made to allow primary-care physicians to more timely use diagnostic devices previously predominately available only in large diagnostic centers. For example, a diagnostic system service provider can lease to a physician a device and charge the physician on a per-test basis, rather than charging a large monthly sum that will require a certain minimum number of tests to reach the break-even point for the physician.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method of diagnosing a medical condition, comprising the steps of:
    initiating an automated test protocol utilizing a test device at a test location;
    generating test data using the test device according to the test protocol, wherein the test data is indicative of performance of a physiological body function;
    transmitting the test data to a medical specialist at a diagnosis center located remotely from the test location, wherein the test location and the diagnosis center are located at different facilities, and wherein the at least a portion of the diagnosis report is transmitted from the diagnosis center to the test location via an intermediate computer located remotely from the test location and the diagnosis center at a different facility;
    generating a diagnosis report based on medical analysis of the transmitted test data by the medical specialist;
    transmitting at least a portion of the diagnosis report to the test location;
    generating a first payment request from the test device indicative of a payment for producing the test data;
    generating a second payment request from a remote computer at the diagnosis center indicative of a payment for providing the diagnosis report; and
    transmitting the first and second payment requests to a billing computer located remotely from both the test location and the diagnosis center at a different facility.

2. The method of claim 1, wherein the step of transmitting the test data to a medical specialist at the diagnosis center comprises transmitting the test data to a remote computer at the diagnosis center, and wherein the method further comprises:
    generating patient identifying data;
    associating a first portion of the patient identifying data with the test protocol; and
    transmitting the first portion of the patient identifying data to the medical specialist at the diagnosis center along with the test data.

3. The method of claim 1 and further comprising:
    storing information on types of tests the test device is capable of making;
    storing information on a plurality specialists, the plurality of specialists including the medical specialist; and
    determining diagnostic work flow with the intermediate computer as a function of the stored information on the types of tests and the plurality of specialists.

4. The method of claim 1 and further comprising the step of:
    generating statistical data with the intermediate computer as a function of the test data transmitted from the test location.

* * * * *